(12) United States Patent
Hewlett

(10) Patent No.: US 6,565,941 B1
(45) Date of Patent: May 20, 2003

(54) MEDIUM FOR A COLOR CHANGER

(75) Inventor: William E. Hewlett, Pasadena, CA (US)

(73) Assignee: Light and Sound Design Ltd., Birmingham (GB)

( * ) Notice: Subject to any disclaimer, the term of this patent is extended or adjusted under 35 U.S.C. 154(b) by 0 days.

(21) Appl. No.: 09/572,045

(22) Filed: May 16, 2000

Related U.S. Application Data

(62) Division of application No. 08/859,770, filed on May 21, 1997, which is a division of application No. 08/790,235, filed on Jan. 28, 1997, now Pat. No. 6,261,636, which is a division of application No. 08/286,929, filed on Aug. 8, 1994, now Pat. No. 5,633,061.

(51) Int. Cl.[7] .............................. B32B 3/02; B41F 5/00
(52) U.S. Cl. ..................... 428/66.6; 428/66.5; 428/141; 428/156; 101/329; 101/348; 492/30; 492/37
(58) Field of Search ................. 428/156, 141, 428/212, 397, 400, 66.6, 66.5; 101/305, 329, 348, 352.11, 375, 352.13; 492/28, 33, 30, 36, 37

(56) References Cited

U.S. PATENT DOCUMENTS

| | | | | |
|---|---|---|---|---|
| 2,638,050 A | * | 5/1953 | King ............................ | 101/375 |
| 3,093,071 A | * | 6/1963 | Taylor ......................... | 101/375 |
| 4,063,828 A | * | 12/1977 | Michael ....................... | 428/367 |
| 4,187,107 A | * | 2/1980 | Homma et al. .............. | 430/252 |
| 4,996,113 A | * | 2/1991 | Hector et al. ................ | 428/600 |
| 5,042,283 A | * | 8/1991 | Wirz ............................ | 101/420 |
| 5,099,759 A | * | 3/1992 | Sonobe et al. .............. | 101/348 |
| 5,126,886 A | * | 6/1992 | Richardson .................. | 359/888 |
| 5,522,786 A | * | 6/1996 | Fields et al. ................. | 492/33 |

* cited by examiner

*Primary Examiner*—Donald J. Loney
(74) *Attorney, Agent, or Firm*—Fish & Richardson P.C.

(57) ABSTRACT

A flexible medium for a scrolling color changer and method of making thereof. The medium is made by applying an ink using a Meyer Rod which has varying cell lengths along its length. This leaves varying size cells of ink at different locations along the length of the medium. The ink has special characteristics whereby its evaporation rate and viscosity are carefully controlled. The viscosity is such that an amount of levelling will occur will be equal to the distance between any cells, but that cell to cell levelling will not, in general, occurs.

2 Claims, 5 Drawing Sheets

| EXAMPLE ONLY | | | |
| --- | --- | --- | --- |
| x = 0 | x = .021 | x = .044 | x = .069 |
| y = 0 | y = .001 | y = .002 | y = .003 |
| r = .010 | r = .011 | r = .012 | r = .013 |

MEDIUM FOR A COLOR CHANGER

This is a divisional of U.S. application Ser. No. 08/859,770, filed May 21, 1997, pending which is a divisional of U.S. application Ser. No. 08/790,235, filed Jan. 28, 1997 now U.S. Pat. No. 6,261,636, which is a divisional of U.S. application Ser. No. 08/286,929, filed Aug. 8, 1994 now U.S. Pat. No. 5,633,061.

BACKGROUND OF THE INVENTION

1. Field of the Invention

The present invention teaches an improved flexible medium for a scrolling-type color changer. More specifically, the present invention defines a color changer medium with continuously-variable characteristics across its length.

2. Background Information

Stage lighting systems project a beam of light which has been colored by a color filter. Different ways of coloring the light are known.

One way of coloring the light is by using dichroic filters such as taught in U.S. Pat. No. 4,800,474. This technique mounts a number of dichroic filters on rotatable color wheels. This system needs a large amount of space because the wheels must each have room for many filters to allow enough colors, and there must be room for the wheels to rotate.

Another way of coloring the light is by using a scrolling type color changer such as that shown and described in U.S. Pat. No. 5,126,886, the disclosure of which is herewith incorporated by reference. Scrolling color changers move material between two scrolls to provide a desired filtering effect within the light path.

A problem occurs in determining how to appropriately change the color across the length of the color media of a scrolling changer. U.S. Pat. No. 5,126,886 demonstrates one conventional method of changing the color saturation across the length of the filter. A filter material is formed with a baseline saturation. A half-tone pattern is located thereof. This half-tone pattern provides a filtering effect which can be changed by adjusting the number of patterned elements per unit area.

SUMMARY OF THE INVENTION

The present invention goes against this established teaching by providing a continuously-varied color media. The color media is formed using a specially designed "Meyer Rod" to adjust the thickness of the coating deposited on the film.

The ink solution according to this invention has special characteristics of viscosity and evaporation rate. The viscosity is controlled such that ink in at least one of the cells flows to the next cell only, and not more than that amount, in the amount of time it takes the ink to dry. This forms a continuous coating that varies in thickness along a gradient axis.

Thicker coatings provide a more saturated color. The thickness of the coating is allowed to vary between cells, but does not vary across the width of the medium.

BRIEF DESCRIPTION OF THE DRAWINGS

These and other aspects of the invention will now be described in detail with reference to the accompany drawings, wherein.

DESCRIPTION OF THE PREFERRED EMBODIMENT

Figure 1:
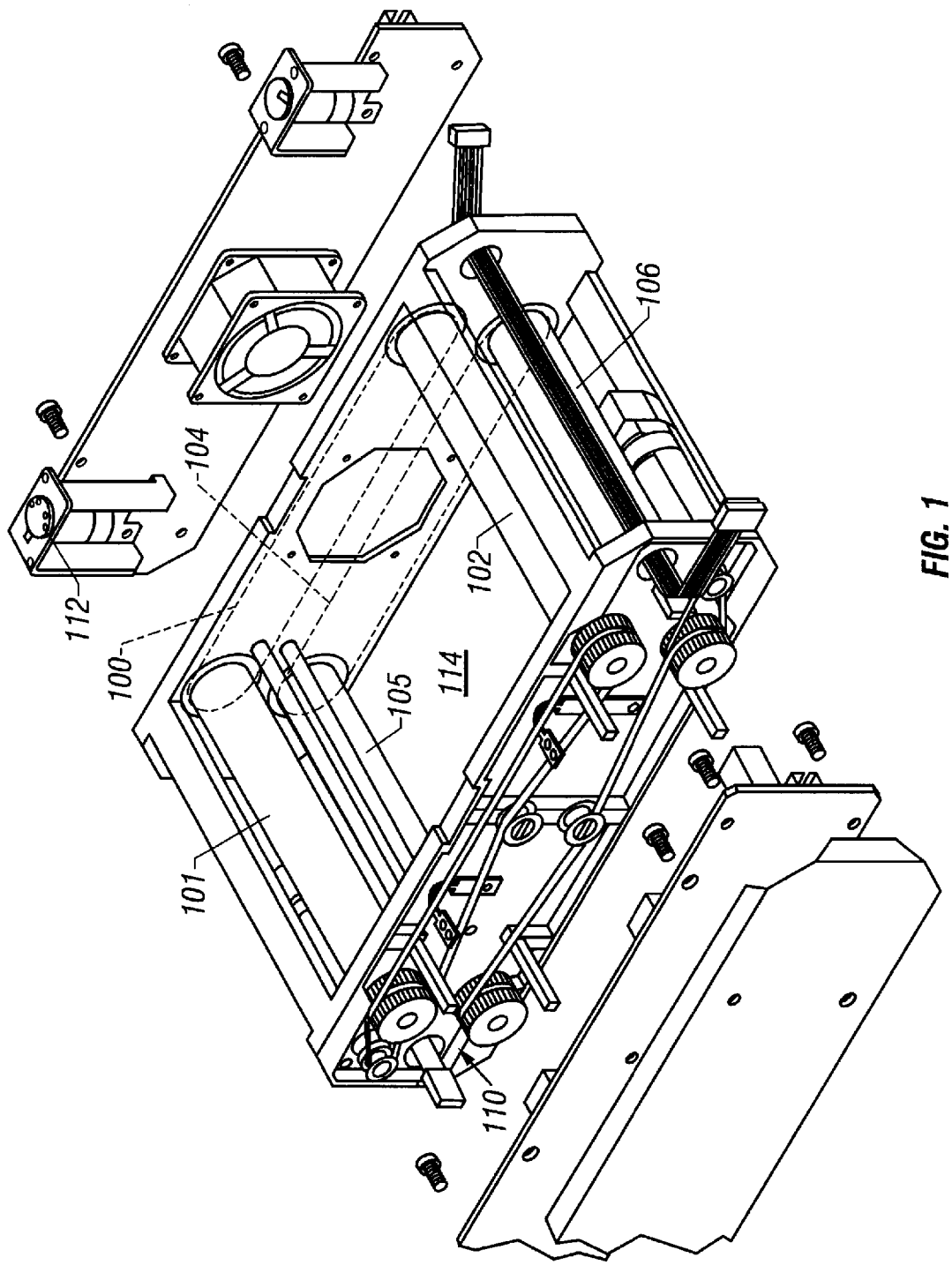
FIG. 1 shows the layout of the basic scrolling color chamber used to hold the medium made according to the present invention.

FIG. 1 shows a basic scrolling color changer according to the present invention. More details about the operation of such a color changer are found in U.S. Pat. No. 5,126,886. The first media 100 of the color changer extends between roll 101 and roll 102. The second media 104 extends between rolls 105 to 106. The two rolls of either pair (101/102 and 105/106) are commonly controlled by gears, e.g., 110, which allows both rolls to move in synchronism. By actuating motor 112, for example, rolls 101 and 102 can be moved to quickly locate the color changer material to a desired location.

The beam of light is shown through location 114, and adjusted by a combination of the two current positions of the scrolls. The color changing capability is obtained by various combinations of the colors in a conventional way.

Figure 2A:
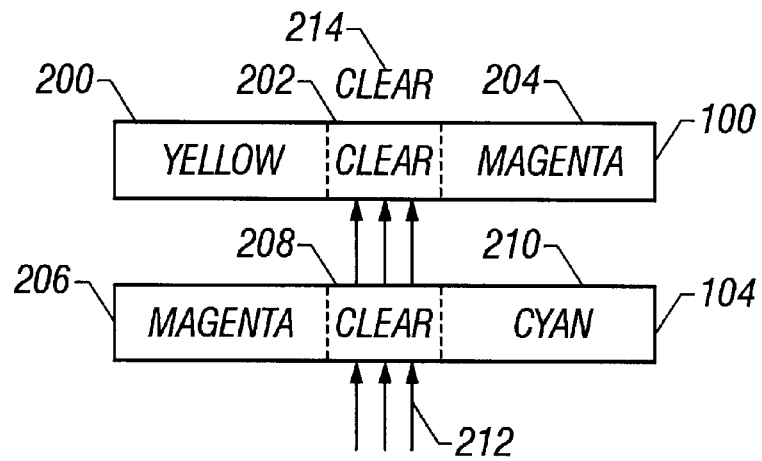
FIGS. 2A–2H show various exemplary locations of the two scrolls used according to the present invention to obtain the most important colors.
Figure 2B:
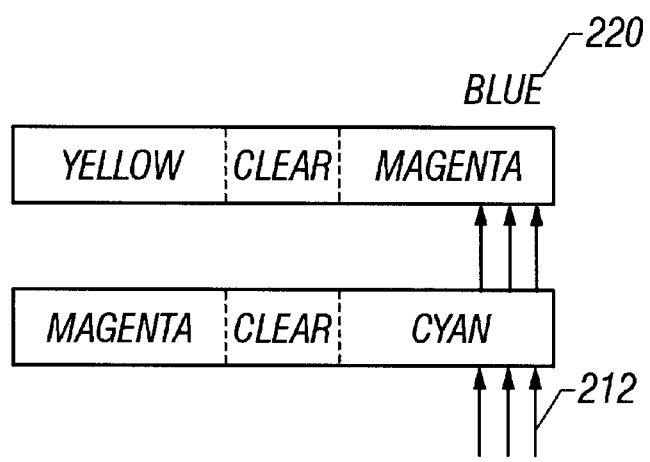
Figure 2C:
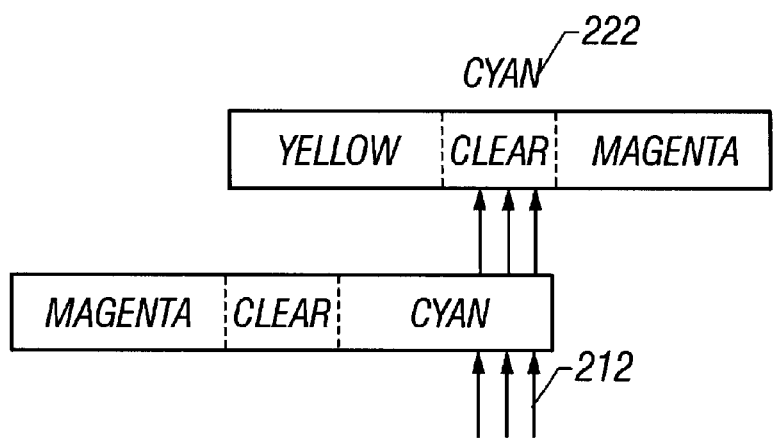
Figure 2D:
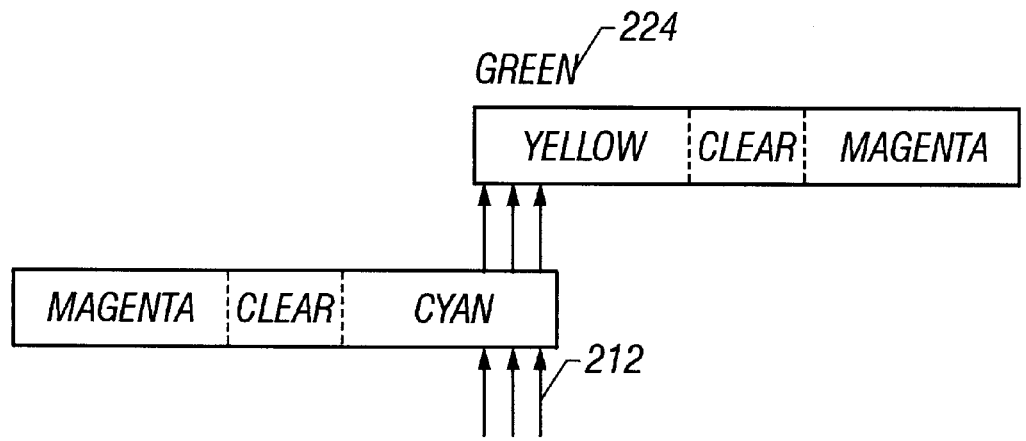
Figure 2E:
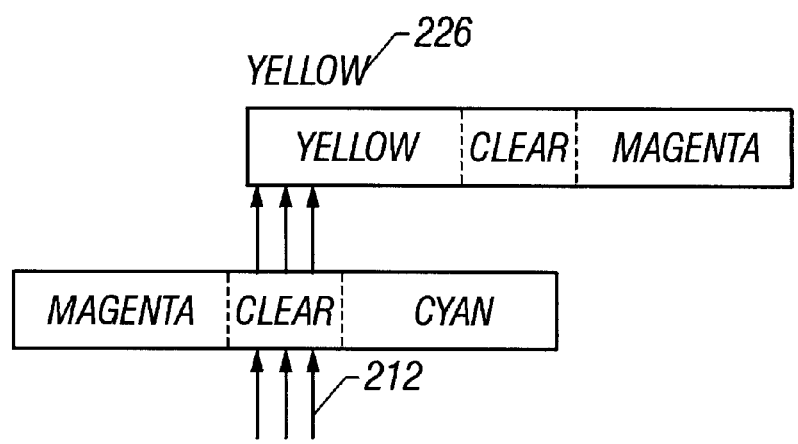
Figure 2F:
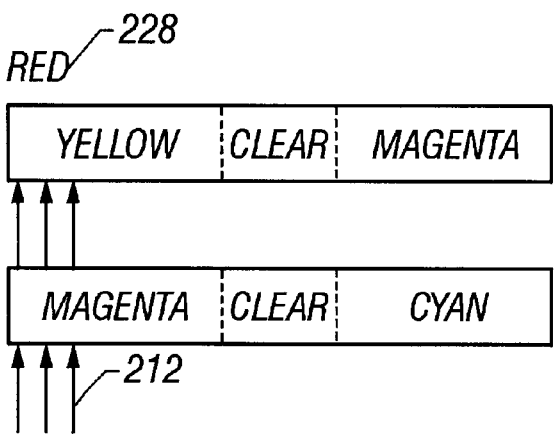
Figure 2G:
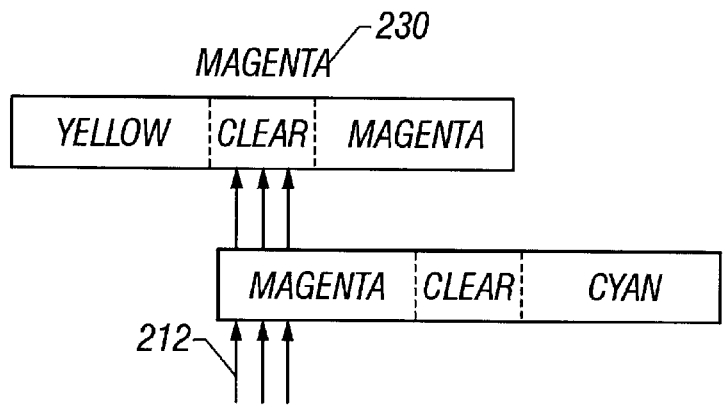
Figure 2H:
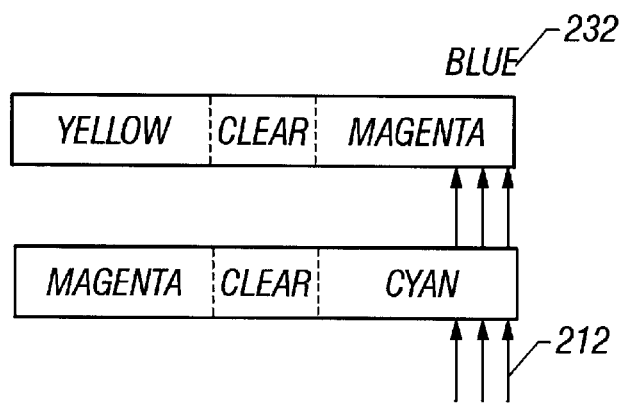

FIGS. 2A–2H show the various ways in which the colors are obtained according to the present invention. Scroll 100 is shown at the top of each of FIGS. 2A–2H, and includes portions with varying saturations of yellow at a first end 200, a clear portion in its center 202, and varying saturations of magenta at a second end 204. The second scroll 104 also includes magenta at a first end 206, is clear in its center 208, and cyan portions at the other end 210. FIG. 2A shows the light beam 212 passing through the two clear portions to obtain a clear light beam 214. FIG. 2B shows how cyan and magenta are combined to obtain blue light beam 220. FIG. 2C shows cyan and clear being combined to obtain cyan light beam 222. FIG. 2D shows cyan and yellow being combined to obtain a green color light beam 224. FIG. 2E shows clear and yellow being combined to obtain a yellow light beam 226. FIG. 2F shows magenta and yellow being combined to obtain red at 22B. FIG. 2G shows magenta and clear being combined to obtain magenta 230, and finally, FIG. 2H shows cyan and magenta being combined to obtain another blue, 232. The scrolls are appropriately positioned to obtain the desired color light.

The actual scroll material is formed of a polycarbonate, polyester or polypropylene film coated with a special colored ink. The colored ink has controlled evaporation and viscosity characteristics which allows continuous coating. For purposes of this specification, the term ink will be used to denote the material which is spread on the polypropylene backing sheet. Ink includes dye molecules, which form the color, in a binder which holds the dye molecules in solution, and a solvent. The ink binder is typically polyester. The dye molecules in the binder gives the material its final color. The solvent keeps the ink in a fluid state until the solvent evaporates. Therefore, when the solvent evaporates, the remaining dye molecules and binder are completely dried.

The polyester binder is in a solvent-based solution. The solvent includes Methyl Ethel Keytone (MEX) and Toluene. The proportion of MEX to Toluene controls the rate of evaporation and levelling of the coating solution. The thickness of the ink on the polyester film controls the saturation of color; the thicker the coating, the more saturated the color becomes.

Any commercially available ink can be used if the viscosity of the solution and rate of evaporation is controlled. The preferred inks used according to the present invention are described herein, The ink is applied in cells as described herein, and the viscosity of the ink solution is controlled such that the amount of ink levelling between cells which occurs in the amount of time that it takes the ink to dry, closely matches the distance between cells. For at least one of the cells, the amount of ink levelling before ink drying is precisely equal to the distance between cells.

The preferred embodiment of the present invention uses a specially-constructed Meyer Rod to apply the ink to the substrate. A prior art Meyer Rod used a stainless steel cylindrical rod with a stainless steel wire wrapped-tightly around its circumference from one end to the other end. The space between adjacent wires holds ink. The amount of the coating deposit depends on the wire diameter or gauge. Typically, the coating is applied to the substrate by passing the substrate through a vat of ink solution, and then using different Meyer Rods to squeegee off all but the amount between the wires if the Meyer rod as the film passes by it. The space between the wire curvatures allows a specific amount of the solution to remain, and thereby leaves cells of material on the substrate. Different wire gauge Meyer Rods leave a different amount of solution on the substrate. Each Meyer Rod left a different thickness of material.

Figure 3:
FIG. 3 shows the preferred technique of applying the material to the substrate according to the present invention.

The present invention uses a Meyer Rod of a special type to spread the ink along the substrate material in a way that it continuously varies along a gradient axis thereof. I considered the idea of forming a Meyer Rod with varying diameter wire. However, I determined that constructing a Meyer Rod that used a length of wire with changing gauge would not be practical by itself since it would produce a conical rod which got larger as the gauge of the wire increased. I therefore decided to machine or precision grind a rod directly from stainless steel, simulating the changing wire curvature, but compensating for the changing radius to end up with a cylindrical form. I therefore invented the Meyer Rod which is shown in FIG. 3 with a cross-section along the line 4—4 being shown in FIG. 4.

Figure 4:
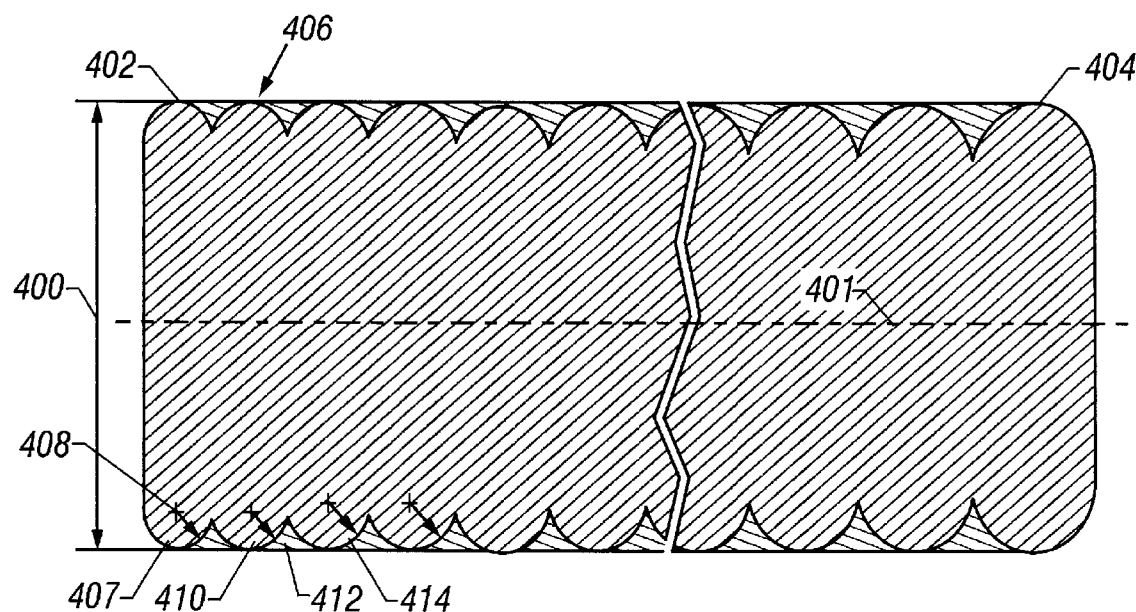
FIG. 4 shows a cross-sectional view of the Meyer Rod of FIG. 3 along the line 4—4.

FIG. 4 shows the overall diameter 400 of the rod which stays the same from-its leftmost end 402 to its rightmost end 404. Overall diameter here refers to the diameter of the outermost edge of each section 406 relative to the central axis 401. However, the diameter of the various sections 406 vary from one end to the other. Each of the sections 406 is defined by three coordinates: x, y, and r. The origin is, for example, shown at point 408, in the center of the a smallest section 407. Hence, the section 407 has x, y coordinates 0,0, and a radius r of 0.10. The second Meyer Rod section 410 is at position 0.021, 0.001 with a radius 0.011. These values are just exemplary, and for a six inch rod, I would start with a radius of 0.025 inch, and increment each successive radius by 0.001 inch.

The Meyer Rod operates by allowing ink to remain only in the interstices 412 between two successive Meyer Rod portions, e.g. 410 and 414. As the portions get larger in radius, the amount of ink left by the interstices also gets larger. This means that the portions of ink deposited by the Meyer Rod at end 402 are smaller than the portions deposited at the end 404. Each portion of ink left by the area between two successive Meyer Rod sections will be referred to herein as a cell.

Figure 5:
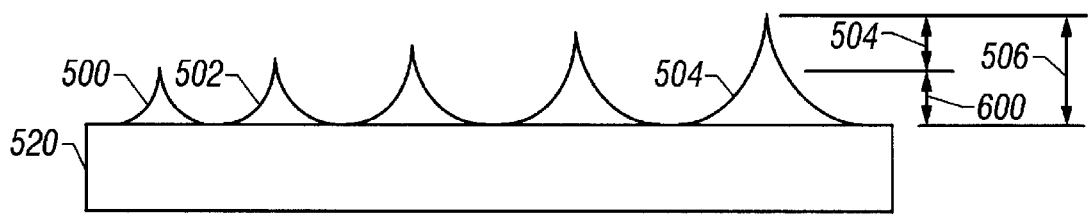
FIG. 5 shows the interim product showing cells of ink on the substrate after the Meyer Rod has passed but before the cells have had time to level.

After the, Meyer Rod has passed, the interim product is as shown in FIG. 5. A number of cells of ink remain on substrate 520. Each successive cell is slightly different in volume than the next cell. For example, Cell 502 has slightly more volume than cell 500. Of course, FIG. 5 shows an exaggeration of this phenomena.

Figure 6:
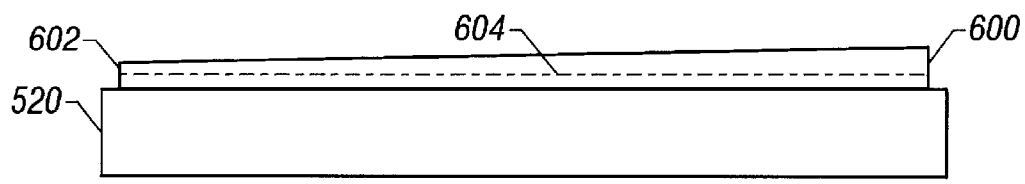
FIG. 6 shows the final levelled product.

According to the present invention, I select inks which have a viscosity such that the amount of levelling between cells in the time it takes the ink to dry is equal to the levelling necessary for the two largest cells. More generally, however, the viscosity must be such that the amount of levelling in the time it takes the ink to dry is equal to the distance be tureen any t-do desired cells Height 600 shows the finally-levelled height at the highest end. Therefore, in the amount of time it takes the ink to dry, levelling by an amount of distance shown as 508, the distance between the highest level 504 and the final height 600, must occur. This may allow some cell-to-cell levelling in the smaller portions such as 500 and 502. However, this trade-off allows all portions to level somewhat, but still to form a material which is thicker at end 600 than it is at 602. It is most important that the cell-to-cell levelling be minimized so that the thickness, and hence color saturation, varies along the gradient axis 604. FIG. 6 shows the portions after levelling.

The characteristics of the ink are therefore crucial. The viscosity of the ink material is proportional to the solid content, to the dye and to the binder. It is also proportional to a ratio between the solids and the binder. The binder is typically a polyester material, such as Vitel (TM). I have used two preferred solvents, one of which is a combination of MEK and Toluene. The ratio between these two controls the amount of evaporation which occurs. I have also used a propylacetate solvent.

According to the present invention, the properties of the ink are controlled such that its viscosity is controlled relative to its evaporation time to provide a controlled amount of levelling. FIG. 6 shows the finally levelled product. In FIG. 6, the discontinuous portions such as 500 and 502 have been smoothed into a continuous portion. The height 600 is also shown in FIG. 5. The height 504 of portion 506 must be decreased by an amount 508 to level the final material at the height 600. Therefore, the viscosity of the material must be such that it can level by an amount 508 in the amount of time it takes for the solvent to evaporate. Some example formulations are described herein:

YELLOW:

The "solids" portion of the yellow ink solution have the following make up:

8.5%—Yellow pigment 83 (C-1. #21108)
91.5%—Binder (Polyester Resin)

The "solvents" portion of the yellow ink solution has the following make up:

1.60%—Ethyl Alcohol
15.62%—Ethyl Acetate
21.67%—Toluene
21.97%—Isopropyl Alcohol
39.14%—Isopropyl Acetate The "solids" and "solvents" are combined in the ratio of:

25.91%—Solids (pigment/binder)
74.09%—Solvents

This solution will have a viscosity of 57 seconds measured with 822.

CYAN:

The "solids" portion of the cyan ink solution has the following make up:

10.1%—Blue 15: 4 (C. I. #74160)
0.1%—Violet 23 (C. I. #51319)
89.8%—Binder (Polyester Resin)

The "solvents" portion of the cyan ink solution has the following make up:

0.26%—Ethyl Alcohol
0.30%—Ethyl Acetate
1.73%—Isopropyl Alcohol
24.63% Toluene
73.08%—Isopropyl Acetate The "solids" and "solvents" are combined in the ratio of:

27.55%—Solids (pigment/binder)
72.45%—Solvents

This solution will have a viscosity of 37 seconds measured with 822.

MAGENTA:

The "solids" portion of the magenta ink solution has the following make up:

9.6%—Rabine Red (C. I. #28620)
91.4%—Binder (Polyester Resin)

The "solvents" portion of the magenta ink solution has the following make up:

0.24%—Ethyl Alcohol
0.32%—Ethyl Acetate
1.54%—Isopropyl Alcohol
23.50%—Toluene
74.40%—Isopropyl Acetate The "solids" and "solvents" are combined in the ratio of:

28.30%—Solids (pigment/binder)
71.70%—Solvents

This solution will have a viscosity of 65 seconds measured with #2Z.

Although only a few embodiments have been described in detail above, those having ordinary skill in the art will certainly understand that many modifications are possible in the preferred embodiment without departing from the teachings thereof.

All such modifications are intended to be encompassed within the following claims.

Although the present invention has been described using a Meyer Rod, it should be understood that other techniques of ink imprintation of a backing material, including but not limited to a gravure cylinder and the like, could also be used for depositing the ink, so long as the ink is applied in cells, and allowed to level between the cells.

What is claimed is:

1. A printing rod, comprising:

a printing element, having an outer surface with a substantially constant radius cylindrical form, said cylindrical form including a plurality of independent ink holding cells therein, each of said ink holding cells formed from an intersection between two substantially arc shaped portions, and an outermost section of said arc shaped portions forming said cylindrical form of said substantially constant radius; and at least a plurality of said cells having a different volume then other ones of said cells, and a first cell at one end of said printing element having a different volume then a second cell at another end of said printing element.

2. A printing rod as in claim 1, wherein each of said ink holding cells has a different volume than each other ink holding cells.

\* \* \* \* \*